(12) United States Patent
Ciupik (10) Patent No.: US 9,707,017 B2
(45) Date of Patent: Jul. 18, 2017

(54) INTERSPINOUS PROCESS SPACER IMPLANT (71) Applicant: Lechoslaw Franciszek Ciupik, Zielona Gora (PL)

(72) Inventor: Lechoslaw Franciszek Ciupik, Zielona Gora (PL)

( * ) Notice: Subject to any disclaimer, the term of this patent is extended or adjusted under 35 U.S.C. 154(b) by 0 days.

(21) Appl. No.: 14/920,707

(22) Filed: Oct. 22, 2015

(65) Prior Publication Data
US 2016/0183987 A1 Jun. 30, 2016

(51) Int. Cl.
*A61B 17/70* (2006.01)
*A61F 2/44* (2006.01)

(52) U.S. Cl.
CPC ...... *A61B 17/7065* (2013.01); *A61B 17/7068* (2013.01); *A61F 2/4405* (2013.01)

(58) Field of Classification Search
CPC ............ A61B 17/7065; A61B 17/7068; A61B 17/7053; A61B 17/7071; A61B 17/7067; A61B 2017/0256; A61F 2/4405
USPC .......... 606/246–279, 86 A; 623/17.11–17.16
See application file for complete search history.

(56) References Cited

U.S. PATENT DOCUMENTS

| | | | |
|---|---|---|---|
| 8,246,655 B2 | 8/2012 | Jackson et al. | |
| 2011/0118788 A1 | 5/2011 | Hochschuler et al. | |
| 2011/0313458 A1* | 12/2011 | Butler | A61B 17/7065 606/249 |
| 2012/0277796 A1 | 11/2012 | Gabelberger et al. | |
| 2014/0228885 A1* | 8/2014 | Dinville | A61B 17/7065 606/249 |

FOREIGN PATENT DOCUMENTS

| | | | | |
|---|---|---|---|---|
| WO | 2008098054 A2 | 8/2008 | | |
| WO | WO2008098054 | * | 8/2008 | ......... A61B 17/7065 |
| WO | 2012030141 A2 | 3/2012 | | |
| WO | 2013109363 A1 | 7/2013 | | |
| WO | WO2013109363 | * | 7/2013 | ......... A61B 17/7065 |

OTHER PUBLICATIONS

European Search Report from EP Application No. Ep 14460077.2 1506 (dated May 4, 2015).

* cited by examiner

*Primary Examiner* — Pedro Philogene (74) *Attorney, Agent, or Firm* — Hovey Williams LLP (57) ABSTRACT An interspinous process spacer implant includes first and second bodies each equipped with upper and lower projections. The implant also includes a hinge connecting central parts of the bodies to one another. The hinge allows the bodies to rotate relative to one another in a forward direction. The implant further includes an arresting mechanism that acts between the central parts of the bodies to block reverse rotation of the bodies relative to one another.

18 Claims, 9 Drawing Sheets

INTERSPINOUS PROCESS SPACER IMPLANT

The present application claims the benefit of and priority from European Patent Application No. EP 14460077, filed Oct. 23, 2014, the entire disclosure of which is hereby incorporated by reference herein.

BACKGROUND

1. Field

The present invention relates to an interspinous process spacer implant for being implanted between spinous processes of neighboring vertebrae.

2. Discussion of Prior Art

Spinal traumata or diseases can lead to spine conditions in which the relative positions of neighboring vertebrae are such that a person experiences pain. For treating such conditions spacer implants are positioned between the spinous processes of the neighboring vertebrae to prevent from relative motion between the two vertebrae. Typical implants are, for example, disclosed in U.S. Pat. No. 8,246, 655 B2 and EP 2 117 470 B1 and WO 2013/109363 A1.

EP 2 117 470 B1 describes an intervertebral implant with a first body and a second body which are hinged together by means of an off-center hinge. The first body includes an upper bearing surface for contacting an upper spinous process which bearing surface is located between two upper projections extending from the first body. Likewise, the second body includes a lower bearing surface for contacting a lower spinous process which bearing surface is located between two lower projections extending from the first body. The first and second bodies also include contact surfaces where the bearing surfaces and the contact surfaces are located at opposite ends of the respective body. The first and second bodies can be rotated about the hinge until the contact surfaces come into contact. The bodies are then fixed in this configuration by an arresting mechanism.

WO 2013/109363 A1 describes an intervertebral implant with a first body and a second body which are hinged together by means of a central hinge. A first body includes a first upper surface and a first lower surface, where a first upper projection and a first lower projection extend from the first upper surface and the first lower surface, respectively. A second body includes a second upper surface and a second lower surface where a second upper projection and a second lower projection extend from the second upper surface and the second lower surface, respectively. The first lower surface is provided with a plurality of ribs which can cooperate with a screw which can be screwed through a threated a through hole in the second lower projection. When the screw is screwed through the through hole the tip of the screw reaches the ribs and thereby secures the first and second bodies relative to each other against rotation about the hinge at a desired distance between the first and second upper projections.

Sometimes it is not sufficient to fix neighboring vertebrae relative to each other. In these cases it might be necessary to enlarge the space between neighboring vertebrae in order to release pressure from spinal nerve routes. Intervertebral implants which allows for distracting neighboring vertebrae are, for example, disclosed in US 2011/0118788 A1, US 2012/0277796 A1 and and WO 2013/0277796 A1. The intervertebral implants disclosed in these documents allow for distracting vertebrae by expanding the implant. Once the desired distracting is achieved the implants are fixed in their expanded configuration by means of screws.

SUMMARY

The following brief summary is provided to indicate the nature of the subject matter disclosed herein. While certain aspects of the present invention are described below, the summary is not intended to limit the scope of the present invention.

Embodiments of the present invention provide an interspinous process spacer implant that does not suffer from the problems and limitations of the prior art devices set forth above.

With respect to the mentioned state of the art it is an objective of embodiments of the present invention to provide an advantageous interspinous process spacer implant for being implanted between spinous processes of neighboring vertebrae.

This objective is achieved by an interspinous process spacer implant as claimed in claim 1. The depending claims contain further developments of the inventive interspinous process spacer implant.

An inventive interspinous process spacer implant for being implanted between spinous processes of neighboring vertebrae comprises a first body and a second body which are hinged together.

The first body includes a first central part which extends over a first length in a first longitudinal direction and a first height in a first transverse direction perpendicular to said first longitudinal direction. Moreover, the first central part has an upper bearing surface for contacting an upper one of the spinous processes and a first lower bearing surface for contacting a lower one of the spinous processes where the first lower bearing surface is located at a distance in the first transverse direction from the first upper bearing surface. The first body is equipped with a first upper projection extending upwards from the first upper bearing surface of the first central part and with a first lower projection extending downwards from the first lower bearing surface of the first central part, where the first upper projection and the first lower projection are located in opposite longitudinal sections of the of the first central part. It shall be noted that the terms "upper" and "lower" relate to the orientation of the implant when it is implanted into a human body. After implanting it into human body the implant is located between neighboring vertebrae where one of the vertebrae is a lower vertebra and the other one an upper vertebra when the person is standing upright. An upper or lower face or upper or lower section or part of the implant is, thus, a face, section or part of the implant which shows towards the upper one of the two vertebrae after implantation when the person bearing the implant stands upright. Likewise, any lower face, section or part of the implant is meant to be a face, section or part which shows towards the lower one of the two vertebrae after implantation when the person wearing the implant is standing upright. Typically, the inventive implant will be symmetric so that any upper surface, section or part of the implant may as well be a lower surface, section or part of the implant or vice versa if the implant is rotated by 180°. Hence, the terms "upper" and "lower" are merely used for distinguishing opposite sites of the implant rather than for defining an orientation in which the implant is to be implanted.

The interspinous process spacer implant also comprises a second body with a second central part which extends over a second length in a second longitudinal direction and a second height in a second transverse direction perpendicular to said second longitudinal direction. The second central part has a second upper bearing surface for contacting the upper one of the spinous processes and a second lower bearing surface for contacting the lower one of the spinous process where the second lower bearing surface is located at a distance in the second transverse direction from the second upper bearing surface. The second body is equipped with a second upper projection extending upwards from the second upper bearing surface of the second central part and with a second lower projection extending downwards from the second lower bearing surface of the second central part, where the second upper projection and the second lower projection are located in opposite longitudinal sections of the second central part.

A hinge is connecting the first central part and the second central part to one another. This hinge is located off-center in the first and second longitudinal directions in each of the first and second central parts. It allows rotating the first body and the second body relative to one another in a forward direction about a rotation axis extending perpendicular to said first and second longitudinal directions and perpendicular to said first and second transverse directions to vary an angle between the first and second longitudinal directions. The hinge is located in the first central part in the longitudinal section where the upper projection extends upwards from the first upper bearing surface. In the second central part, the hinge is located in the longitudinal section where the second lower projection extends downwards from the second lower bearing surface.

In addition, the inventive interspinous process spacer implant comprises an arresting mechanism acting between the first central part and the second central part for blocking a reverse rotation of the first and second bodies relative to one another. This arresting mechanism provides at least a first arrest position for preventing a reverse rotation when the first and second bodies are in a rotational position relative to one another in which the longitudinal directions of the first and second central parts include a first angle between 0° and 30°. In addition, the arresting mechanism provides a second arrest position for preventing a reverse rotation when the first and second bodies are in a rotational position relative to one another in which the longitudinal directions of the first and second central parts include a second angle between 0° and 30° where the second angle differs from the first angle. The first angle, i.e. the angle that is included by the first and second longitudinal directions of the first and second central bodies when the first and second bodies are in the first arrest position, may in particular be 0°. Then the second angle, i.e. the angle between the longitudinal directions of the first and second central parts when the first and second bodies are in the second arrest position, is larger than 0°, for example 10° or 20°.

The inventive interspinous process spacer implant allows for fixing neighboring vertebrae with different distances between them. The different distances are defined by the different arresting positions, in which the angles between the longitudinal directions of the central parts differ from one another. If the angle is small, the distance between the bearing surfaces is also small. For example, if the upper bearing surface and the first lower bearing surface extend in said first longitudinal direction substantially parallel to each other and the second upper bearing surface and the second lower bearing surface extend in said second longitudinal direction substantially parallel to each other and the first height and the second height are identical the distance between the upper and lower bearing surfaces would be given by this height if the angle between the first and second longitudinal directions is 0°. On the other hand, when the angle between the longitudinal directions of the central parts is larger than 0° the second upper bearing surface will be lifted above the first upper bearing surface. At the same time, the first lower bearing surface will be moved below the second lower bearing surface. As a consequence, the distance between the second upper bearing surface and the first lower bearing surface increases which leads to a distraction of the neighboring vertebrae. Hence, by choosing the arresting position of the implant the distraction state of the neighboring vertebrae between which the implant is introduce can be set.

Since in the first arrest position and the second arrest position a reverse rotation of the first and second body relative to one another, which could be a result of the spinours processes pressing on the bearing surfaces is blocked the vertebrae are fixed in the respective distraction state once the implant has been brought into the first or second arrest position. It is, therefore, not necessary to fix the configuration of the implant by means of screws for keeping the neighboring vertebrae in their distraction state.

In addition to the first and second arrest positions the arresting mechanism may provide at least one additional arrest position for preventing a reverse rotation when the first and second bodies are in a rotational position relative to one another in which the longitudinal directions of the first and second central bodies include an angle between 0° and 30° which is different from the first angle and from the second angle. By this measure, at least a third distraction state of the neighboring vertebrae between which the implant is introduced can be provided. For example, in the first arrest position, the angle between the first longitudinal direction and the second longitudinal direction may be 0°, in the second arrest position, 15° and in the first arrest position, 30°. However, it shall be noted, that other sequences of angles are also possible. In addition, they may also be more than three arrest positions, for example one arrest position in which the angle between the longitudinal directions of the central parts is 0°, one in which the angle between the longitudinal directions is 10°, one in which the angle between the longitudinal directions is 20° and one in which the angle between the longitudinal directions is 30°. However, in many cases two arrest positions are sufficient.

A solid design of the inventive interspinous process spacer implant can be achieved if the first body has a larger width than the second body and a recess of a defined width is provided in the first central part and in the first lower projection of the first body where the recess extends in the first longitudinal direction and the first transverse direction. Then, the second central part and the second upper projection each have a width allowing them to fit into the recess. In this design, the hinge can be realized by an axle extending through the recess in the central body and through the other one of the central bodies. As an alternative, the width of the second body may be larger than the width of the first body and the recess of a defined may be provided in the second central part and in the second upper projection. Then, the first central part and the first lower projection each have a width allowing them to fit into the recess.

In the mentioned solid design of the inventive interspinous process spacer implant the arresting mechanism may include at least one notch and at least one protrusion that fits into said notch. The notch or the protrusion is provided in a wall of the recess and the other one of the notch and the protrusion is provided on a resilient arm extending from the central part with the width that allows it to fit into the recess towards the wall with the notch or the protrusion.

In an advantageous further development of the interspinous process spacer implant the hinge allows the first body and the second body to be in a rotational implanting position in which the first and second longitudinal directions include an angle between −90° and −150° before the first body and the second body are brought into one of the arrest positions. By this measure, it becomes possible to bring the first and the second body into a rotational position relative to one another in which the upper projection of the first body and the lower projection of the second body are oriented parallel to each other or almost parallel to each other while the lower projection of the first body and the upper projection of the second body are oriented such that they converge at a distance from the central parts. In this configuration of the implant, the cross-section of the implant is rather small so that it can be implanted with only a small incision for accessing the space between the spinous processes of the vertebrae to be treated.

The first central part and the second central part of the interspinous process spacer implant may be equipped with indentations that are adapted to receive tips of an implanting instrument. In particular, at least one indentation may be located in the longitudinal section of the first central part which is located opposite to the longitudinal section where the first upper projection extends upwards from the first upper bearing surface and at least one indentation may be located in the longitudinal section of the second central part which is located opposite to the longitudinal section where the second lower projection extends downwards from the second lower bearing surface. The mentioned locations of the indentations allow for bringing the implant from the rotational implanting position of the first and second bodies relative to each other into one of the arrest positions by moving opposite ends of an implanting instrument towards each other.

In order to improve the grip of the first upper projection and the second lower projection about the bone structure of the respective spinous process the first upper projection may include a first upper projection surface emerging from the first upper bearing surface which is equipped with anchoring elements for anchoring the first upper projection in a spinous process. The second lower projection may include a second lower projection surface emerging from the second lower bearing surface which is equipped with anchoring elements for anchoring the second lower projection in the bone structure of a spinous processes.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Preferred embodiments of the invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the preferred embodiments.

DETAILED DESCRIPTION OF THE PREFERRED EMBODIMENTS

In the following, an inventive interspinous process spacer implant will be described with respect to FIGS. 1 to 9. The interspinous process spacer implant comprises a first body, a second body and a hinge by which the first body and the body are connected to one another. The first body will be described with respect to FIGS. 1 and 2 and the second body will be described with respect to FIGS. 3 and 4. The hinge and its function will be described with respect to FIGS. 5 to 9 where FIGS. 6 to 9 show an assembled interspinous process spacer implant in different configurations.

Figure 1:
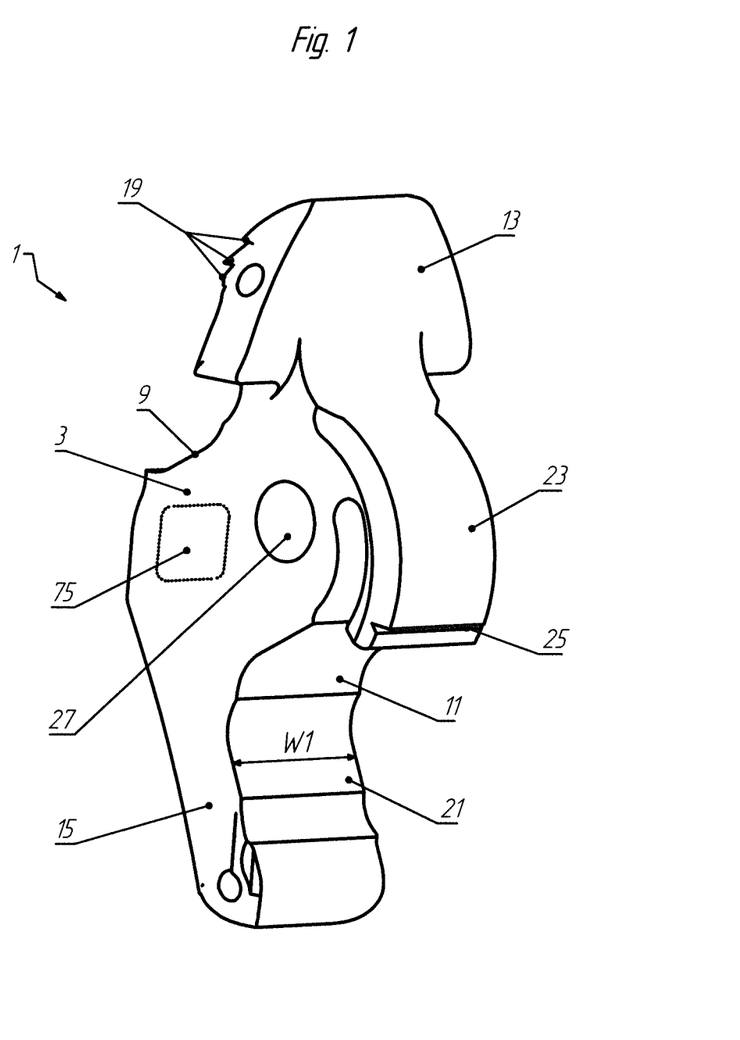
FIG. 1 shows a first body of an inventive interspinous process spacer implant in a perspective view.

The first body 1 of the interspinous process spacer implant comprises a central part 3 which is called first central part 3 in the following to distinguish it from a central part of the second body, which will be described later. The central body 3 has a length l1 along a longitudinal direction 5 (see FIG. 2), called first longitudinal direction 5 in the following, and height h1 in a transverse direction 7, called first transverse direction 7 in the following, which is perpendicular to the first longitudinal direction 5. A first upper bearing surface 9 and a first lower bearing surface 11 are located at transverse opposite ends of the first central body 3, i.e. at ends which are opposite in the first transverse direction 7. The reason why these surfaces are named "upper bearing surface" and "lower bearing surface" will be explained later. The upper bearing surface 9 and lower bearing surface 11 have a distance from each other which corresponds to the height h1 of the first central part 3, i.e. its dimension in transverse direction 7.

Figure 2:
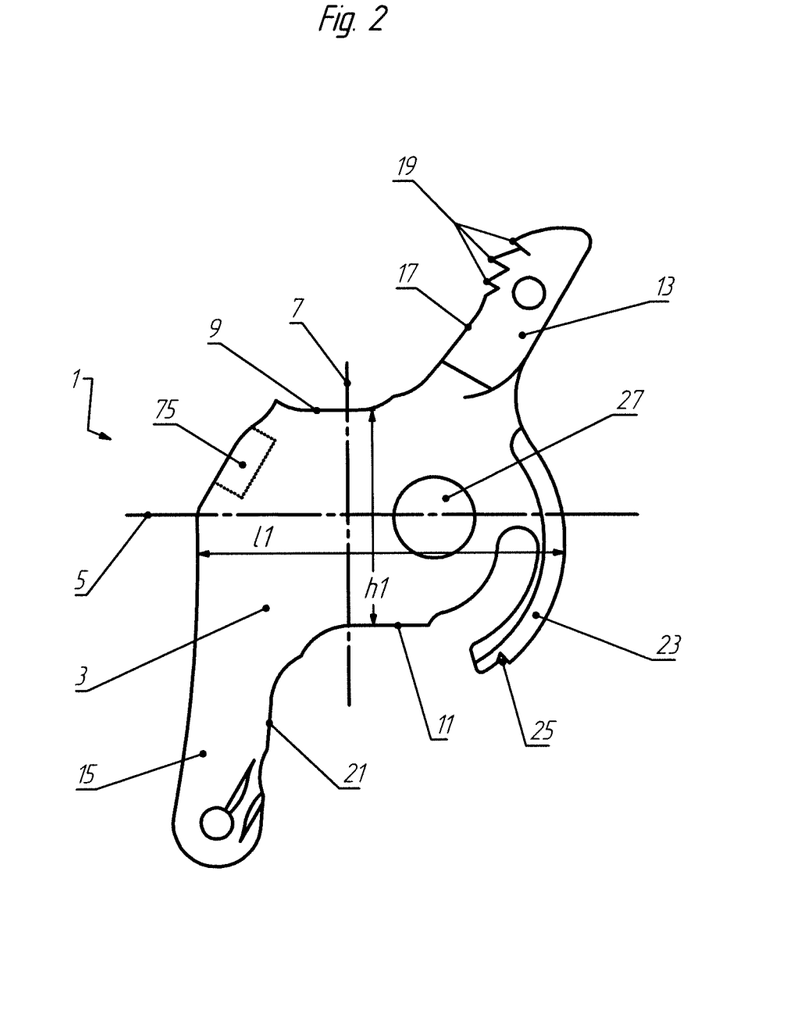
FIG. 2 shows the first body of the implant shown in FIG. 1 in a plan view.

The first body 1 is equipped with a first upper projection 13 and a first lower projection 15. The first upper projection 13 extends upwards from the first upper bearing surface 9 and has a first upper bearing projection surface 17 that emerges from the first upper bearing surface 9. Cutting edges 19 are present in the upper projection surface 17 at the distal end of the upper projection 13. These cutting edges 19 can cut into the bone structure of a spinous process and serve as anchor elements of the interspinous process spacer implant. The first upper projection 13 and the first lower projection 15 are located at opposite longitudinal sections of the first central part and extend more or less linearly from the first central part. While the first upper bearing surface 9 and the first upper projection surface 17 include an angle of about 60° the first lower bearing surface 11 and the first lower projection surface 21 include an angle of about 90°.

In addition to the first upper projection 13 an the first lower projection 15 the first body 1 includes a further projection which extends from the first central part 3. This further projection forms a resilient arm 23 which emerges from the longitudinal section of the first part 3 from which also the first upper projection 13 emerges, and follow a partly circular curvature around the central part 3. At the distal end of the resilient arm 23 there is a notch the meaning of which will be explained later.

The first central part 3 and the first lower projection 15 both have the same width w1 (see FIG. 1).

A through hole 27 is formed in the first central part 3 which is part for a hinge connection which will be explained later. The trough hole is located in the longitudinal section of the first central part 3 from which also the first upper projection 13 emerges.

Figure 3:
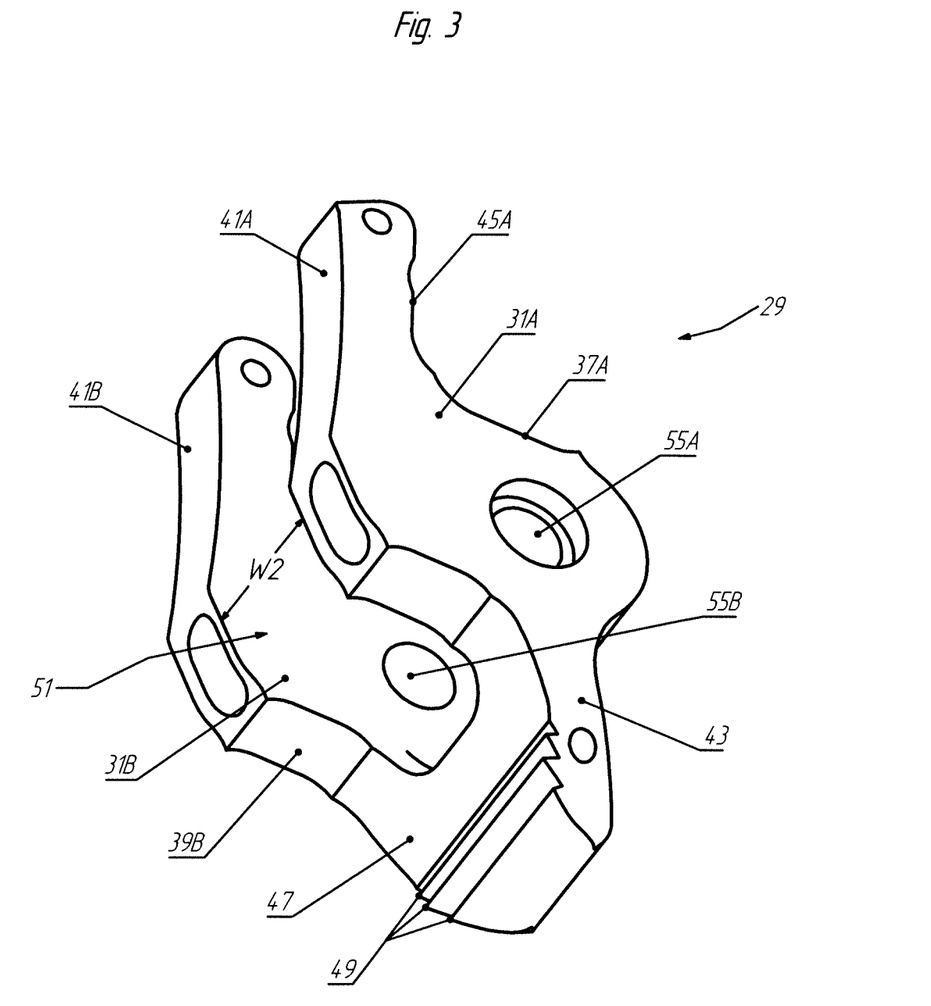
FIG. 3 shows a second body of the inventive interspinous process spacer implant in a perspective view.
Figure 4:
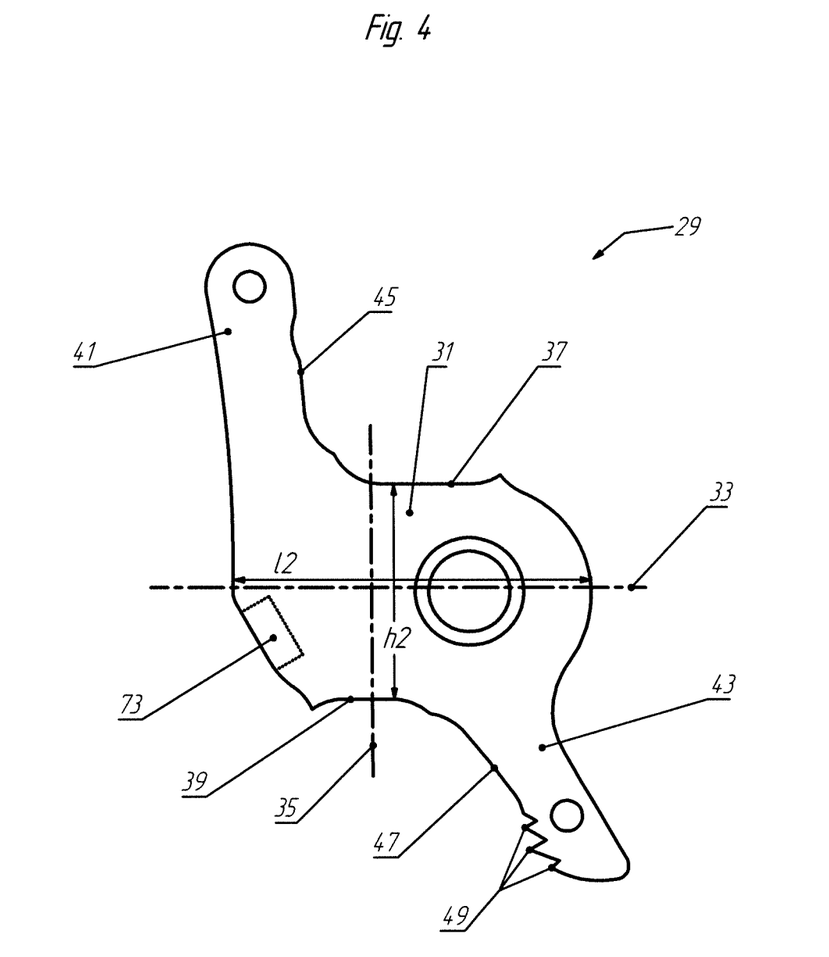
FIG. 4 shows the second body of the implant in a plan view.

The second body of the inventive interspinous process spacer implant will now be described with respect to the FIGS. 3 and 4. Like in the first body 1 of the interspinous process spacer implant the second body 29 of the interspinous process spacer implant comprises a central part 31 which has a length l2 in a second longitudinal direction 33 and a height h2 in a second transverse direction 35 which is perpendicular to the second longitudinal direction 33. The length l2 of the second central part 31 equals the length l1 of the first central part 3. In addition, the height h2 of the second central part 31 equals the height h1 of the first central part 3. The second central part 31 has a second upper bearing surface 37 and second lower bearing surfaces 39 which are located at opposite ends in transverse direction 35 and have a distance from each other which corresponds to the height h2 of the central body 31. Like in the first body 1 the second upper bearing surface 37 and the second lower bearing surface 39 run substantially parallel to each other and to the longitudinal direction 33.

A second upper projection 41 and a second lower projection 43 extend from longitudinal opposite sections of the central part 31. The second upper projection 41 has a second upper projection surface 45 which emerges from the second upper bearing surface 37 and includes an angle with the second upper bearing surface 37 of approximately 90°. The second lower projection 43 has a second lower projection surface 47 which emerges from the second lower bearing surface 39 and includes an angle with the second lower bearing surface 39 of approximately 120°. Cutting edges 49 are present in the second lower projection surface 47 at the distal end of the second lower projection 43.

A recess 51 extends in longitudinal direction 33 and transverse direction 35 from the distal end of the second upper projection 41 through the second upper projection 41 and the second central part 31. This recess 51 has a width w2 which corresponds to the width w1 of the first central part 3 and the first lower projection 15 and divides the second central part 31 and the second upper projection 41 into two parts 31A, 31B and 41A, 41B. Hence, the second body 29 resembles a fork-like structure with two blades where the first blade is formed by the second central part 31A and the second upper projection 41A on one side of the recess and the second blade is formed by the second central part 31B and the second upper process 45B at the other side of the recess 51. These blades are connected to each other by means of the second lower projection 43, which is not recessed and forms a crown of the fork-like structure.

The second lower projection 43 includes a wall which shows towards the recess 51 and delimits the recess against the second lower projection 43. A protrusion 53, which is not visible in FIGS. 3 and 4, is present in this wall of the second lower projection 43. Please note that the protrusion can be seen in FIGS. 8 and 9.

Through holes 55A, 55B are present in the longitudinal section of the second central part 31A, 31B from which the second lower projection 43 extends. These through holes 55A, 55B are present in the two blades of the fork-like structure and are centered relative to one another. Moreover, the through holes 55A, 55B are located such that the through hole 27 of the first central part 3 can be centered relative to the through holes 55A, 55B in the second central part 31 when the first central part 3 is located in the recess 51 of the second central part 31.

Figure 5:
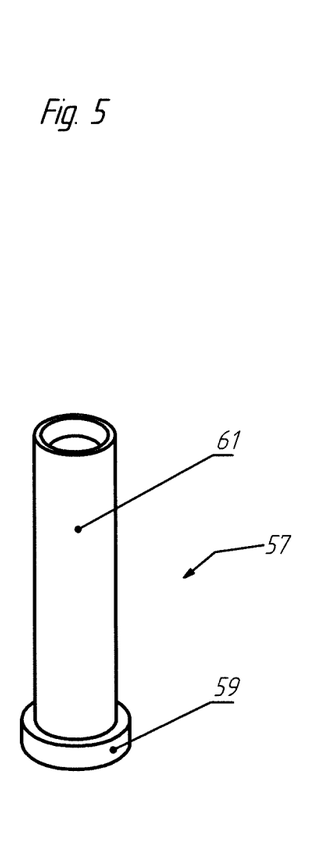
FIG. 5 shows a pin for forming an axle of a hinge connecting the first body and the second body.

A pin 57 with a head 59 and a shaft 61 can be put through the through holes 27, 55A, 55B in the first and second central parts 3, 31a, 31B to form an axle for a hinged connection between the two bodies 1, 29. The head 59 of the pin 57 rests in a slightly enlarged section of the through hole 55A in one of the blades of the second body 29.

When the interspinous process spacer implant is assembled, i.e. the first body 1 is inserted with its first central part into the recess 51 of the second body 29 and the first and the second central parts 3, 31A, 31B are connected to each other by mans of the pin 57, the shaft 61 of the pin 57 provides an axle of a hinge. By means of the hinge, the first body 1 and the second body 29 can be rotated relative to one another about the axle formed by the shaft 61 of the pin 57. This allows the interspinous process spacer implant to be at least in the configurations shown in FIGS. 6 to 9. While FIGS. 6 and 7 show a configuration which is used for inserting the implant between spinous processes of neighboring vertebrae FIGS. 8 and 9 show configurations of the implant which are used to fix the vertebrae relative to each other.

Figure 6:
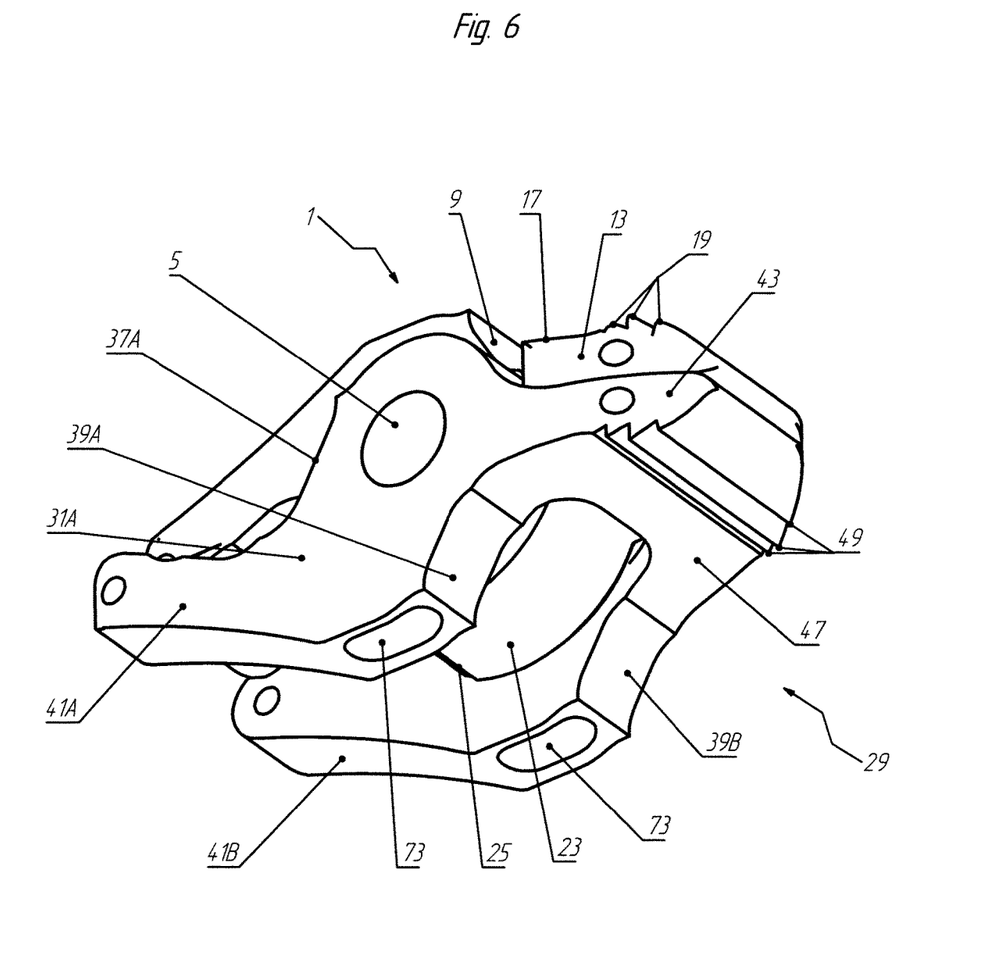
FIG. 6 shows the inventive interspinous process spacer implant in a configuration for inserting it between spinous processes of neighboring vertebrae in a perspective view.
Figure 7:
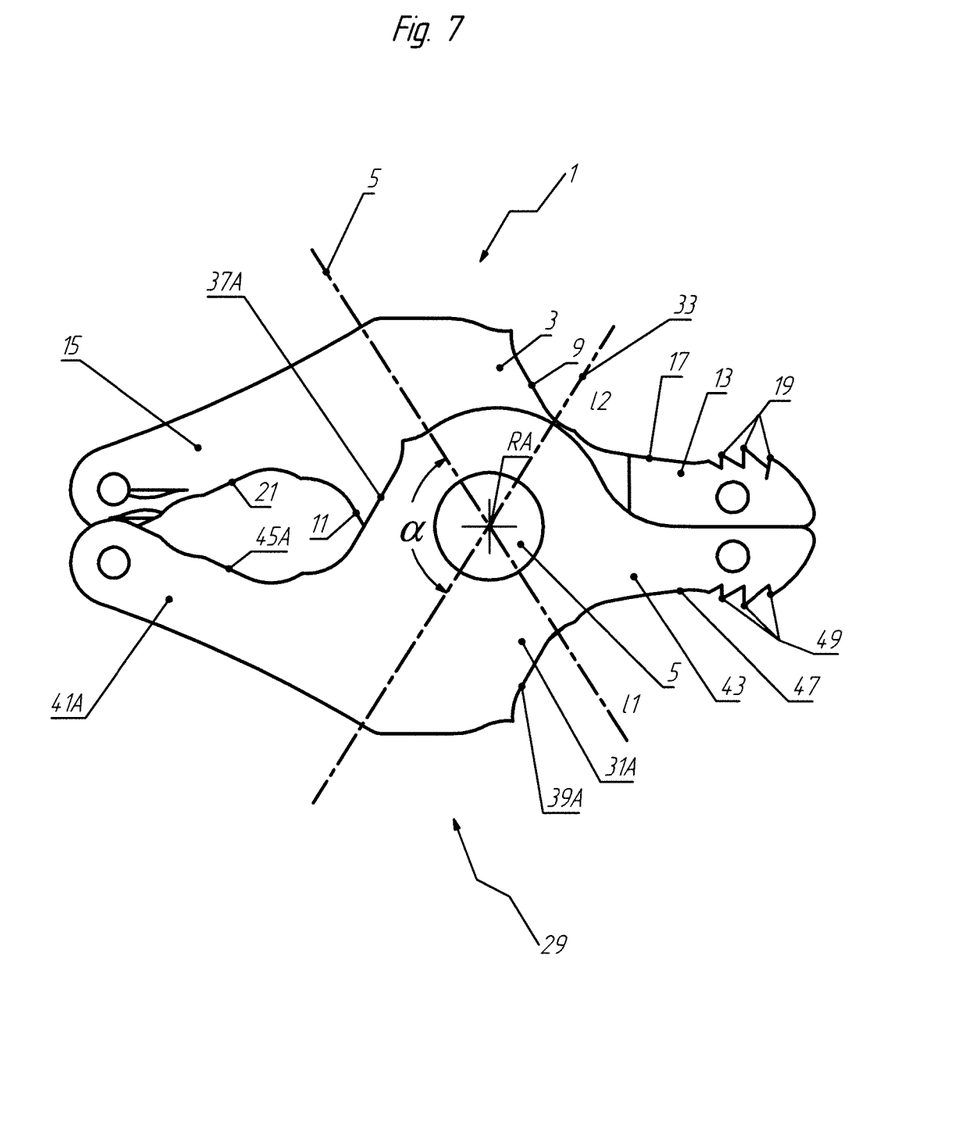
FIG. 7 shows the configuration of FIG. 6 in a plan view.

In the configuration shown in FIGS. 6 and 7 the longitudinal directions 5, 33 include an angle of 120°. As a result, the first upper projection 17 and the second lower projection 43 abut each other and run parallel to each other. At the same time, the first lower projection 15 and the second upper projection 41 form an apex with their distal ends when viewing the implant in the direction of the axis of rotation. In this configuration, the interspinous process spacer implant has a relative small cross section when it is moved in a direction extending from the apex to the parallel first upper projection 17 and second lower projection 43 which allows it to be inserted between the spinous processes of neighboring vertebrae through a relatively small incision. Hence, the configuration shown in FIG. 7 can be seen as an implanting configuration with a rotational implanting position of the bodies relative to each other.

After the interspinous process spacer implant has been positioned between the interspinous processes of neighboring vertebrae the first body 1 and the second body 29 are rotated about a rotation axis RA given by the shaft 1 of the pin 5 relative to each other such that the angle decreases and eventually becomes 0°. This configuration is shown in FIG. 8 in a plan view in which the second body 29 is partly cut in order to show the resilient arm 23 with the notch 25 of the first body and the protrusion 53 in the wall of the second lower projection 41.

Figure 8:
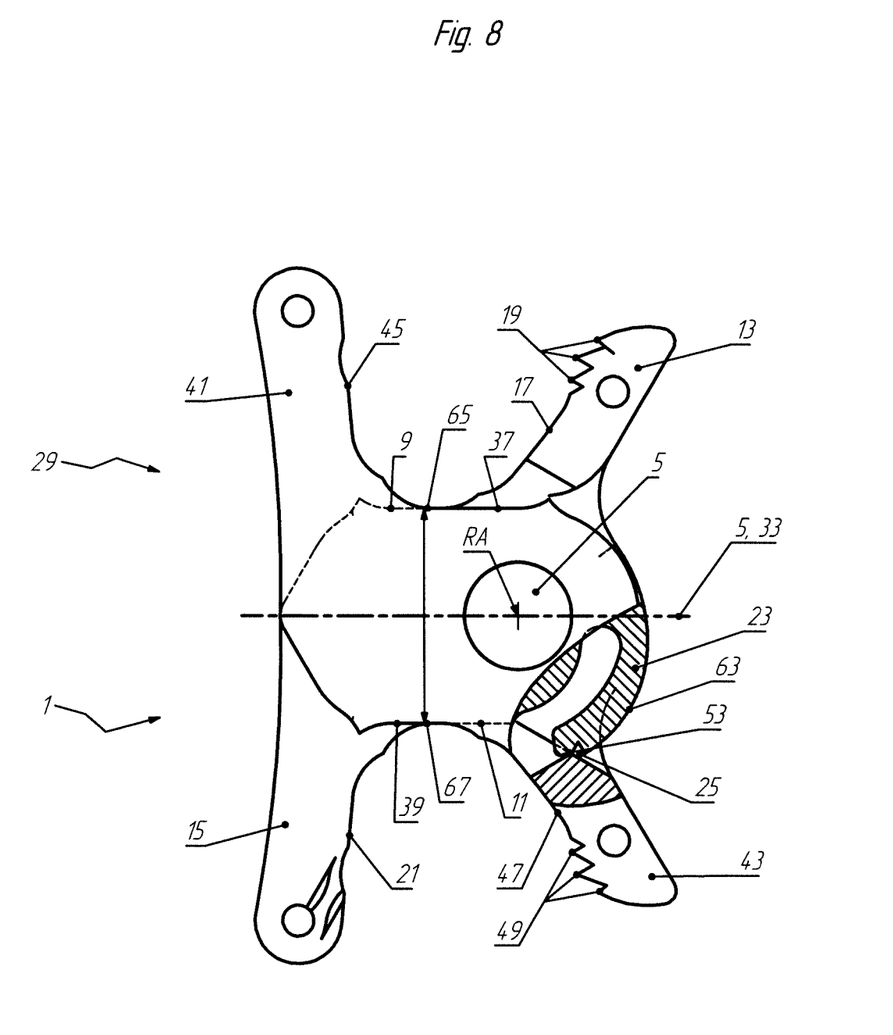
FIG. 8 shows the inventive interspinous process spacer implant in a first arrest position in a plan view.
Figure 9:
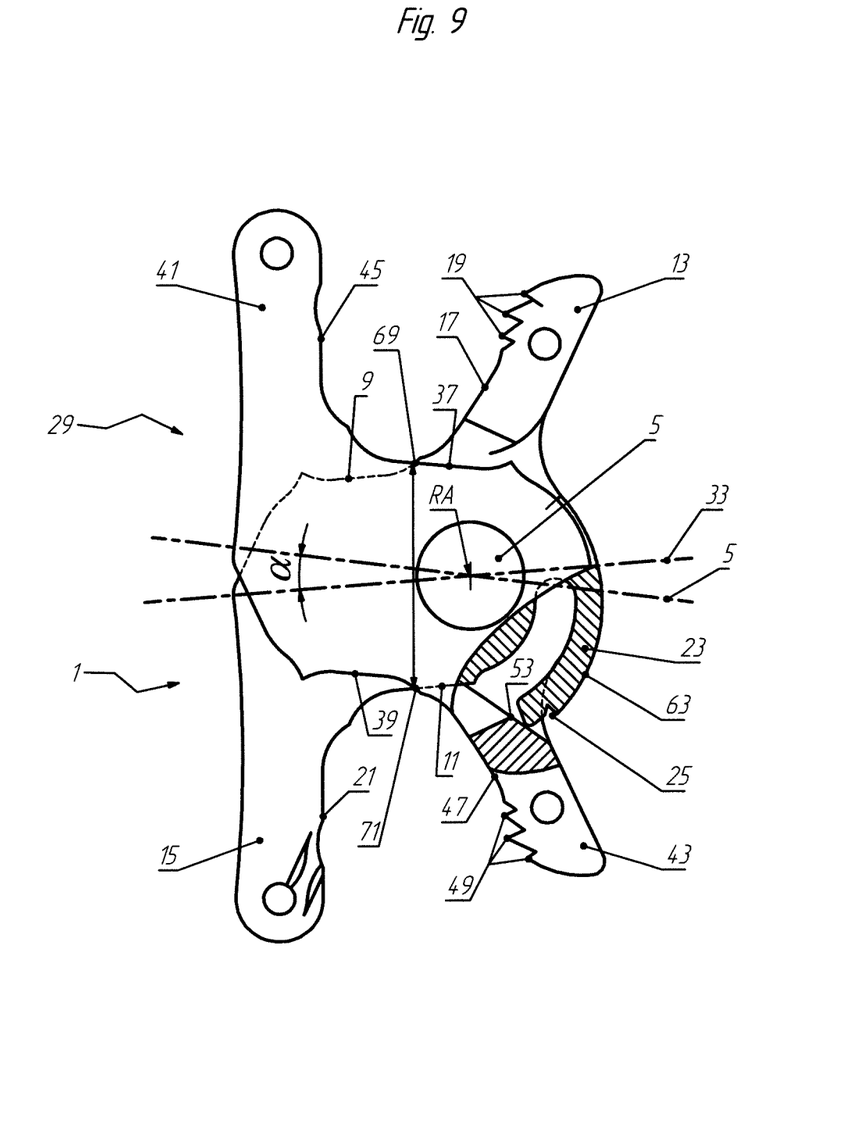
FIG. 9 shows the inventive interspinous process spacer implant in a second arrest position in a plan view.

The configuration shown in FIG. 8 is a first configuration which is used for fixing neighboring vertebrae. In this configuration, a spinous process of an upper one of the neighboring vertebra comes to rest on the first upper bearing surface 9 and the second upper bearing surface 37 while a spinous process of a lower vertebra comes to rest on the first lower bearing surface 11 and the second lower bearing surface 39. Therefore, the bearing surfaces have been named upper and lower bearing surface. Of course, it would be possible to implant the spinous process spacer implant in an orientation which is rotated by 180° with respect to the orientation shown in FIG. 8. In this case, the upper bearing surfaces would be lower bearing surfaces and the lower bearing surfaces would be upper bearing surfaces. Therefore, the names upper bearing surface and lower bearing surface shall not be understood in a limiting, sense, i.e. in a sense, that it is necessary that the respective surface shows upwards or downwards, respectively. Instead, the naming shall only distinguish the surfaces from each other.

In the configuration shown in FIG. 8 the longitudinal directions 5, 33 run parallel to each other, i.e. the angle between the longitudinal directions 5, 33 is 0°. The implant is arrested in this configuration by means of the notch 25 in the resilient arm 23 and the protrusion 53 present in the wall of the second lower projection 53. During the rotation which brings the implant from the configuration shown in FIGS. 6 and 7 into the configuration shown in FIG. 8 the protrusion 53 slides along the outer surface 63 of the resilient arm 23 thereby pressing the resilient arm inwards, i.e. towards the first central part 3. Once, the configuration shown in FIG. 8 is reached the resilient arm 23 moves outwards again so that the protrusion 53 snaps into the recess 25. In this state, the recess 25 and the protrusion 53 prevent the first body 1 and the second body 29 from rotating in reverse direction so that the implant is arrested in the shown configuration when forces acting on the upper projections 13, 41 and the lower projections 15, 43 which tend to spread the projections. Since, by this means, the bodies 1, 29 of the implant are prevented from rotating backwards into the configuration shown in FIGS. 6 and 7 the implant can fix neighboring vertebrae even if considerable forces act on the upper projections 13, 41 and/or the lower projections 15, 43. Hence, the resilient arm 23 with the notch 25 and the protrusion 53 in the wall of the second lower projection 43 can be seen as an arresting mechanism acting between the first central part and the second central part for blocking a reverse rotation of the first and second bodies relative to one another.

However, the geometry of the notch 25 is such that a further forward rotation of the first and second body 1, 29 relative to one another about the rotation axis RA is not prevented. When the first body 1 and the second body 29 are rotated further in forward direction a configuration is reached in which the first longitudinal direction 5 and the second longitudinal direction 33 include an angle which is about 10°. In this configuration, the protrusion 53 is free from the resilient arm 23. However, the resilient arm prevents from a reverse rotation about the rotation axis RA which would tend to decrease and angle again. Hence, the first and second bodies 1, 29 are prevented from rotating backwards either into the configuration shown in FIG. 8 or the configuration shown in FIGS. 6 and 7.

In the configuration shown in FIG. 8 the distance between the points 65, 67 on which the spinous processes rest corresponds to the distance between the upper bearing surface and the lower bearing surface in the first and the second body 1, 29 of the implant (because the heights of h1, h2 of their central parts 3, 31 are equal to each other). On the other hand, in the configuration shown in FIG. 9 the distance between the points 69, 71 on which the spinous processes come to rest is increased due to the rotation of the central parts 3, 31 relative to one another. As a consequence, the inventive interspinous process spacer implant can be adapted to different distances between the spinous processes of neighboring vertebrae, or the inventive interspinous process spacer implant can be used to distract the vertebrae by using either the configuration shown in FIG. 8 or the configuration shown in FIG. 9.

Please note that the angle shown in FIG. 9 is reached by a forward rotation starting from the configuration shown in FIG. 8 (which represents an angle of 0°) while the angle shown in FIGS. 6 and 7 is reached by a reverse rotation starting from the configuration shown in FIG. 8. In this sense, the angle of 120° can be seen as a negative angle of −120° as compared to the angle of 10° in the configuration shown in FIG. 9.

The inventive implant may be brought from the configuration shown in FIGS. 6 an 7 into the configuration shown in FIG. 8 or into the configuration shown in FIG. 9 by means of an instrument having tips which can be moved towards each other and which can engage longitudinal sections of the central parts 3, 31 which lay opposite to the longitudinal sections in which the through holes for the pin 5 are located. In the present embodiment, an indentation 75 is present the first central part 3 which indentation can receive a first tip of an implanting instrument. Similar indentations 73A, 73B are present in the blade like parts of the second central part 31A, 31B where in each blade like part, one of the indentations 73A, 73B is located in a longitudinal section which lies opposite to the longitudinal section with the through holes for the pin 5. By pressing the tips of the instrument together when the tips are located in the indentations a rotation from the configuration shown in FIG. 7 into the configuration shown in FIG. 8 can be effected. Pressing the tips further together effects a further rotation from the configuration shown in FIG. 8 into the configuration shown in FIG. 9.

The present invention has been described in detail with reference to a particular embodiment. However, a person skilled in the art conceives that one can depart from features described with respect to the embodiment. For example, the upper and lower bearing surfaces of the central parts do not need to be substantially parallel to each other. Moreover, the angles the upper and lower process surfaces include with the respective upper and lower bearing surfaces may differ from what has been described in the embodiment. In addition, a person skilled in the art sees that it is possible to provide more than one notch 25 in the resilient arm 23. This leads to the provision of additional arrest positions for preventing a reverse rotation of the first and second body relative to one another. As a consequence, it is possible to increase the number of configurations with different distances between the points at which the spinous processes come to rest. Therefore, the present invention shall not be limited to a combination of features of the described embodiment but only by the appended claims.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. An interspinous process spacer implant for being implanted between spinous processes of neighboring vertebrae, said interspinous process spacer implant comprising:
   a first body with a first central part which extends over a first length in a first longitudinal direction and a first height in a first transverse direction perpendicular to said first longitudinal direction and which has a first upper bearing surface for contacting an upper one of the spinous processes and a first lower bearing surface for contacting a lower one of the spinous processes where the first lower bearing surface is located at a distance from the first upper bearing surface in the first transverse direction, the first body being equipped with a first upper projection extending upwards from the first upper bearing surface and with a first lower projection extending downwards from the first lower bearing surface, where the first upper projection and the first lower projection are located in opposite longitudinal sections of the of the first central part;
   a second body with a second central part which extends over a second length in a second longitudinal direction and a second height in a second transverse direction perpendicular to said second longitudinal direction and which has a second upper bearing surface for contacting the upper one of the spinous processes and a second lower bearing surface for contacting the lower one of the spinous processes where the second lower bearing surface is located at a distance from the second upper bearing surface in the second transverse direction, the second body being equipped with a second upper projection extending upwards from the second upper bearing surface of the second central part and with a second lower projection extending downwards from the second lower bearing surface of the second central part, where the second upper projection and the second lower projection are located in opposite longitudinal sections of the of the second central part;
   a hinge connecting the first central part and the second central part to one another which is located off-center in the first and second longitudinal directions in each of the first and second central parts and allows rotating the first body and the second body relative to one another in a forward direction about a rotation axis extending perpendicular to said first and second longitudinal directions and perpendicular to said first and second transverse directions to vary an angle between the first and second longitudinal directions, where the hinge is located in the first central part in the longitudinal section where the first upper projection extends upwards from the first upper bearing surface and in the second central part in the longitudinal section where the second lower projection extends downwards from the second lower bearing surface; and
   an arresting mechanism acting between the first central part and the second central part for blocking a reverse rotation of the first and second bodies relative to one another about the rotation axis, the arresting mechanism providing at least a first arrest position for preventing a reverse rotation when the first and second bodies are in a rotational position relative to one another in which the longitudinal directions of the first and second central parts include a first angle between 0° and 30° and a second arrest position for preventing a reverse rotation when the first and second bodies are in a rotational position relative to one another in which the longitudinal directions of the first and second central parts include a second angle between 0° and 30° where the second angle differs from the first angle,
   one of said first body and said second body including a resilient arm and the other one of said first body and said second body including a protrusion, with the resilient arm and protrusion cooperatively providing the arresting mechanism,
   said resilient arm and said protrusion being engaged with each other in each of the first and second arrest positions to restrict said reverse rotation while permitting forward rotation,
   said upper bearing surfaces and said lower bearing surfaces defining, respectively, upper and lower contact points on which the corresponding spinous processes are adapted to rest, with a contact distance between the contact points associated with a spinous process distance between the spinous processes,
   said resilient arm and said protrusion permitting, in each of the first and second arrest positions, the contact distance to be increased by rotating the first and second bodies relative to one another in the forward direction.

2. The interspinous process spacer implant as claimed in claim 1, in which the first angle is 0° and the second angle is larger than 0°.

3. The interspinous process spacer implant as claimed in claim 1,
   said arresting mechanism providing at least one additional arrest position for preventing a reverse rotation when the first and second bodies are in a rotational position relative to one another in which the longitudinal directions of the first and second central bodies include an angle between 0° and 30° which is different from the first angle and from the second angle.

4. The interspinous process spacer implant as claimed in claim 1,
   said first upper bearing surface and said first lower bearing surface extending in said first longitudinal direction substantially parallel to each other,
   said second upper bearing surface and said second lower bearing surface extending in said second longitudinal direction substantially parallel to each other.

5. The interspinous process spacer implant as claimed in claim 1; and
   a recess of a defined width being provided in the second central part and in the second upper projection where the recess extends in the second longitudinal direction and the second transverse direction, and the first central part and the first lower projection each have a width allowing them to fit into the recess, or said recess being provided in the first central part and in the first lower projection where the recess extends in the first longitudinal direction and the first transverse direction, and the second central part and the second upper projection each have a width allowing them to fit into the recess.

6. The interspinous process spacer implant as claimed in claim 1,
   said hinge allowing the first body and the second body to be in a rotational implanting position in which the first and second longitudinal directions include an angle between than −90° and −150° before the first body and the second body are brought into one of the arrest positions.

7. The interspinous process spacer implant as claimed in claim 1,
   said first central part and said second central part being equipped with indentations which are adapted to receive tips of an implanting instrument.

8. The interspinous process spacer implant as claimed in claim 7,
- at least one of said indentations being located in the longitudinal section of the first central part which is located opposite to the longitudinal section where the first upper projection extends upwards from the first upper bearing surface and at least one of said indentations being located in the longitudinal section of the second central part which is located opposite to the longitudinal section where the second lower projection extends downwards from the second lower bearing surface.

9. The interspinous process spacer implant as claimed in claim 1,
- said first upper projection including a first upper projection surface emerging from the first upper bearing surface and the second lower projection includes a second lower projection surface emerging from the second lower bearing surface where the first upper projection surface and the second lower projection surface are equipped with anchoring elements for anchoring the first upper projection and the second lower projection in the bone structure of opposing spinous processes.

10. The interspinous process spacer implant as claimed in claim 2,
- said hinge allowing the first body and the second body to be in a rotational implanting position in which the first and second longitudinal directions include an angle between than −90° and −150° before the first body and the second body are brought into one of the arrest positions.

11. The interspinous process spacer implant as claimed in claim 2,
- said arresting mechanism providing at least one additional arrest position for preventing a reverse rotation when the first and second bodies are in a rotational position relative to one another in which the longitudinal directions of the first and second central bodies include an angle between 0° and 30° which is different from the first angle and from the second angle.

12. The interspinous process spacer implant as claimed in claim 5, in which the first angle is 0° and the second angle is larger than 0°.

13. The interspinous process spacer implant as claimed in claim 5,
- said arresting mechanism providing at least one additional arrest position for preventing a reverse rotation when the first and second bodies are in a rotational position relative to one another in which the longitudinal directions of the first and second central bodies include an angle between 0° and 30° which is different from the first angle and from the second angle.

14. The interspinous process spacer implant as claimed in claim 5,
- said first upper bearing surface and said first lower bearing surface extending in said first longitudinal direction substantially parallel to each other,
- said second upper bearing surface and said second lower bearing surface extending in said second longitudinal direction substantially parallel to each other.

15. The interspinous process spacer implant as claimed in claim 5,
- said hinge allowing the first body and the second body to be in a rotational implanting position in which the first and second longitudinal directions include an angle between than −90° and −150° before the first body and the second body are brought into one of the arrest positions.

16. The interspinous process spacer implant as claimed in claim 5,
- said first central part and said second central part being equipped with indentations which are adapted to receive tips of an implanting instrument.

17. The interspinous process spacer implant as claimed in claim 16,
- at least one of said indentations being located in the longitudinal section of the first central part which is located opposite to the longitudinal section where the first upper projection extends upwards from the first upper bearing surface and at least one of said indentations being located in the longitudinal section of the second central part which is located opposite to the longitudinal section where the second lower projection extends downwards from the second lower bearing surface.

18. The interspinous process spacer implant as claimed in claim 5,
- said first upper projection including a first upper projection surface emerging from the first upper bearing surface and the second lower projection includes a second lower projection surface emerging from the second lower bearing surface where the first upper projection surface and the second lower projection surface are equipped with anchoring elements for anchoring the first upper projection and the second lower projection in the bone structure of opposing spinous processes.

* * * * *